United States Patent [19]
Maldonado et al.

[11] 3,986,933
[45] Oct. 19, 1976

[54] METHOD OF PREPARING YEASTS ENRICHED IN L-LYSINE AND CAPABLE OF EXCRETING ORGANIC ACIDS

[75] Inventors: Paul Maldonado, St Symphorien D'Ozon; Claude Gaillaridin, Paris; Gaëtan Sylvestre, Epernon; Georges Glikmans, Meudon La Foret, all of France

[73] Assignee: Institut Francais du Petrol, des Carburants et Lubrifiants et Entreprise de Recherches et d'Activities Petrolieres Elf, Paris and Rueil Malmaison, France

[22] Filed: Apr. 21, 1975

[21] Appl. No.: 569,616

[30] Foreign Application Priority Data
Apr. 23, 1974 France .............................. 74.14094

[52] U.S. Cl. ................................ 195/28 R; 195/79
[51] Int. Cl.$^2$ ............................................ C12B 1/00
[58] Field of Search ............... 195/28 R, 30, 36, 37, 195/47, 82, 76, 97, 112, 79

[56] References Cited
UNITED STATES PATENTS
3,660,235   5/1972   Okumura et al. ..................... 195/37
3,825,472   7/1974   Kubota et al. ........................ 195/28 R
3,873,424   3/1975   Kimura et al. ........................ 195/36 R

*Primary Examiner*—A. Louis Monacell
*Assistant Examiner*—R. B. Penland

[57] ABSTRACT

A method of preparing a yeast enriched in L-lysine and capable of excreting an organic acid, such as citric acid, and possibly also isocitric and glutamic acids, when cultivated on a hydrocarbon-containing medium comprises subjecting a yeast of the species *Candida lipolytica* to the action of a mutagenic agent, such as a chemical agent or radiation, cultivating the thus-treated yeast in a culture medium containing a lysine analogue, preferably that to which the original yeast is most sensitive, in a concentration which is about 50 to 100 times greater than that to which the cells of the original yeast are most sensitive, and cultivating the resultant mutated resistant yeast on a medium containing at least one hydrocarbon such as a $C_{10}$–$C_{20}$ normal paraffin as well as conventional nutrients, the cultivation preferably being effected in an agitated aerated medium at a pH of 3 to 6 and a temperature of 25° to 30° C.. The yeast enriched in L-lysine may be recovered from the reaction medium as a useful product and citric acid and other acids may be recovered in conventional manner from the reaction medium.

11 Claims, No Drawings

METHOD OF PREPARING YEASTS ENRICHED IN L-LYSINE AND CAPABLE OF EXCRETING ORGANIC ACIDS

BACKGROUND OF THE INVENTION

This invention relates to the preparation of novel strains of yeast and to the use thereof for simultaneously preparing by fermentation a biological material which is enriched in L-lysine and which may be used as food, and citric acid.

Yeasts of the species Candida lipolytica are known and have been grown on hydrocarbon-containing substrates.

It has now been found that yeasts of the species Candida lipolytica can be mutated to produce new strains which are resistant to lysine analogues which, in low concentrations, are normally toxic to these yeasts.

When the strains acquire the aforementioned resistance, there is a considerable increase in the lysine intracellular ratio and they can simultaneously excrete appreciable quantities of citric and isocitric acids in a fermentation medium containing hydrocarbons and mineral salts in non-limiting quantities, without it being necessary to add any compound capable of producing one or other of these acids during fermentation.

SUMMARY OF THE INVENTION

Accordingly the present invention provides a method of preparing a yeast enriched in L-lysine and capable of excreting an organic acid, comprising the steps of subjecting a yeast of the species Candida lipolytica to the action of a mutagenic agent, cultivating the thustreated yeast in a culture medium containing a lysine analogue in a concentration which is about 50 to 100 times greater than that to which the cells of the original yeast are sensitive to obtain a mutated resistant yeast, and cultivating said resistant yeast on a medium containing at least one hydrocarbon.

The mutagenic agent used in the first step of the present method can be either a chemical agent, such as, for example, nitroso methylurethane (NMU) or nitroso methyl guanidine (NMG), or radiation, such as, for example X rays or ultra violet rays.

During the second step of the present method, cultivation can be carried out in the presence of any lysine analogue. As is known, strains of Candida yeast are sensitive to all lysine analogues, which are therefore called "toxic analogues" by specialists, examples of such toxic analogues including:

amino-cyclohexyl alanine,
transdehydrolysine (T.D.L.),
S($\beta$-amino-ethyl) cysteine,
2,6-diamino-heptanoic acid,
oxalysine,
amino 3-methyl cyclohexane glycine,
aza 4-lysine,
5-methyl lysine,
$\alpha$-amino $\epsilon$-hydroxycaproic acid and
$\delta$-hydroxylysine.

The sensitivity to lysine analogues is such that if a lysine analogue is present in the culture medium for a Candida yeast, the growth of the yeast is completely stopped.

In the second step of the present method, therefore, the yeast obtained in the first step is cultivated in a medium containing a lysine analogue at a relatively high concentration, followed by selection of the yeasts which can grow in the presence of a lysine analogue.

Various yeast strains may not have the same sensitivity to the same analogue, and a given strain need not have the same sensitivity towards all toxic analogues, owing to variations in the permeability of the cell to the analogue.

Accordingly, the sensitivity of a given strain to an analogue used in a given concentration is specific to the strain.

In order to make a strain resistant, it is advantageous to choose the analogue to which the strain is most sensitive, thus eliminating the masking of toxicity by permeability factors and thus obtaining a strain which is subsequently more effective. The reason is, that if a strain has been made resistant to the lysine analogue to which it is most sensitive, it can be normally cultivated in the presence of the other analogues, whereas if any analogue is chosen, it is not certain that the strain can grow in the presence of a more toxic lysine analogue.

The resistance to a lysine analogue of the yeast obtained in the first step is found by spreading the cellular suspension on a gelose nutrient medium containing the lysine analogue at a concentration 50 to 100 times greater than that to which normal cells are sensitive; this concentration is usually equal to at least $10^{-5}$ molar. Only resistant cells are capable of growth.

Alternatively, either of the following tests can be used. The first test consists in measuring, after one day of cultivation on a minimum medium, the quantity of intracellular lysine obtained for each strain, and comparing this quantity with the quantity obtained for the wild strain.

The second test consists in measuring, for each strain, the inhibition of homocitrate synthetase enzyme by lysine; if more than 60% of the enzyme is inhibited, it can be considered that the strain does not grow.

If a mutant strain passes these tests, it is considered suitable.

In the third step of the present method, the resistant yeast selected during the second step is cultivated on a hydrocarbon-containing substrate, so as to obtain a biological material which has been enriched in L-lysine and excretes metabolic products such as citric acid, isocitric acid and/or glutamic acid.

The percentage of lysine with respect to cellular proteins is found to increase greatly during the cell growth phase, which has an advantageous effect on the nutritional quality of the finally-obtained biological material. As is known, L-lysine is an amino acid essential for mammals, and is an important growth factor in young patients. It has also been surprisingly found that if the cells resistant to toxic lysine analogues are grown on n-paraffins, citric acid and isocitric acid are simultaneously and abundantly produced in a fermentation medium not containing any limiting qualities of mineral or organic nutrient materials, whereas the sensitive cells from which the resistant cells were formed excrete very little acid in the same medium and under the same growth conditions.

In order to obtain the excretion of metabolites, it is usual to attempt to stop metabolism by limiting at least one of the nutrient substances in the medium, but not in the present case.

This is an advantage, since, as is known, citric acid is an organic acid which is very widely used in the food, pharmaceutical and detergent industries.

These cells have the property of becoming enriched in L-lysine and excreting citric acid into a nutrient medium containing n-paraffins and under the optimum cultivation conditions for growth. This constitutes another advantage, in that the cells can be continuously produced by one, two or three-step cultivation, and cells rich in lysine on the one hand and a concentrated aqueous solution of citric acid on the other hand can be permanently recovered at the outlet of the last fermentor used in the process, simply by centrifuging.

A thorough analysis of the aqueous solution shows that there is also an appreciable quantity of isocitric acid and a smaller quantity of glutamic acid.

The method can be carried out e.g. by preparing an inoculum of a yeast culture, e.g. *Candida lipolytica*, capable of assimilating n-paraffins, making it resistant to the action of a toxic lysine analogue, using the aforementioned methods of mutagenesis, and carrying out fermentation in the presence of at least one normal paraffin containing 10 to 20 carbon atoms.

The inoculum can be prepared by suspending Candida yeast cells made resistant to a toxic lysine analogue under aerobic conditions in an aqueous medium containing a source of assimilable carbon (usually an industrial fraction of n-paraffin $C_{10}$–$C_{20}$ hydrocarbons) and a source of assimilable nitrogen and agitating the medium at a temperature of 25° to 30° C. for e.g. 36 hours.

After Candida cells have been obtained at sufficient density in the inoculum culture, a part thereof is added to the fermentation medium, which contains a source of n-paraffin carbon, a source of assimilable nitrogen and various cations, anions and vitamins which are known to favour growth.

The source of nitrogen used in the fermentation medium can be, for example, an inorganic ammonium salt, such as ammonium nitrate, ammonium sulphate, ammonium chloride or ammonium carbonate, or an organic material, such as urea.

The following cations and anions also favour the growth of Candida yeasts: potassium, sodium, magnesium, manganese, iron, calcium, copper, cobalt, acid phosphates, sulphates, chlorides, borates, molybdates and nitrates.

As is generally known, the growth of cells is favourably influenced by adding traces of vitamins such as thiamine and biotin to Candida yeast cultures.

After seeding, fermentation is brought about in an agitated, strongly aerated medium at a temperature which is usually from 25° to 35° C., and preferably 30° C., by diffusing sterile compressed air into the fermentation medium at a rate of 0.5 to 1.5 liters of air per minute and per liter of medium.

The pH of the medium containing the growing cells is preferably adjusted so that the multiplication rate of the yeast cells is at the optimum value, i.e. from 3 to 6 and preferably from 4 to 5.

The pH can be regulated e.g. by adding a basic aqueous solution such as an aqueous solution of ammonia, sodium hydroxide, potassium hydroxide, sodium carbonate or potassium carbonate. Preferably, however, the pH is maintained at the desired value by adding an aqueous ammoniacal solution so as to maintain optimum cell growth.

After the yeasts have grown sufficiently and adequate quantities of citric and isocitric acid have accumulated, fermentation is stopped and the medium is centrifuged. The resulting cake of lysine-enriched cells is washed and dried in a manner conventional for processing yeasts for nutritional use, and is then stored.

The concentrated citric acid in the supernatant fluid is isolated by conventional methods, e.g. in the form of its calcium salt. For example, the stoichiometric quantity of calcium chloride required for chelating the citric acid in the solution can be added to the supernatant liquid, followed by neutralisation e.g. by adding an aqueous ammoniacal solution, after which calcium citrate is precipitated by heating to boiling for one hour with agitation.

The citric acid can subsequently be recovered from its calcium salt by processing with sulphuric acid. For example, the salt can be washed in cold water and suspended in water cooled to 5° to 10° C., the suspension being agitated and kept at the same temperature, after which the stoichiometric quantity of sulphuric acid is added for completely releasing the citric acid, i.e. until the pH of the suspension has stabilised at 1.75 to 1.85.

The resulting calcium sulphate is recovered by filtration. The filtrate is conveyed through basic, then acid ion-exchange resin columns to eliminate the mineral impurities remaining in solution, and is then evaporated to dryness at reduced pressure and at a temperature not greater than 35° C., thus recovering the entire crystalline mass of citric acid formed during fermentation.

PREFERRED EMBODIMENTS OF THE INVENTION

The invention will now be explained with reference to the following Examples:

EXAMPLE 1 a. Preparation of Mutants Resistant to Transdehydrolysine (T.D.L.) and Test

The wild strain IFP 29 (ATCC 20-460) of *Candida lipolytica* was cultivated overnight on a solid gelose medium containing yeast extract and glucose. The cells were suspended in sterile distilled water at a density of $10^7$ cells/ml. and 5 ml. of the suspension were placed in a Petri dish (diameter 5 cm.) and irradiated with ultraviolet light (2000 ergs/mm.$^2$) for 1 minute. Fractions, each 0.1 ml., of the cellular suspension were spread on Petri dishes containing a minimum gelose medium supplemented with $5.10^{-4}$ M 4–5 dehydrolysine dihydrochloride (TDL). The medium had the following composition:

A$_2$ salts: 100 ml.
Glucose: 10 g.
Na$_2$HPO$_4$: 3.95 g.
Agar: 20 g. per 1000 ml. distilled water.
Thiamine: 10 ppm.

Composition of A$_2$ salts: KH$_2$PO$_4$ 10 g.
MgSO$_4$.7H$_2$O 5 g.
NaCl 1 g.

|   | -continued | |
|---|---|---|
| $A_1$ salts: | $CaCl_2$ (anhydrous) | 0.75 g. |
| | $H_3BO_3$ | 500 mg. |
| | $CuSO_4.5H_2O$ | 40 mg. |
| | KI | 100 mg. |
| | $FeCl_3.6H_2O$ | 200 mg. |
| | $MnSO_4.4H_2O$ | 530 mg. |
| | $H_2MoO_4.2H_2O$ | 160 mg. |
| | $ZnSO_4.7H_2O$ | 400 mg. per 1000 ml. distilled water. |

After 5 days of incubation at 28° C., a number of resistant colonies were isolated. They grew without difficulty on a medium which was $5.10^{-3}$ M with respect to TDL whereas the wild strain IFP 29 stopped growing completely on a medium which was $5.10^{-5}$ M with respect to TDL. Out of 34 strains isolated (called Mg-1 to Mg-34), 25 grew as well as IFP 29 on glucose and n-hexadecane and were preserved for future research.

These strains were cultivated on a minimum liquid medium (the same as before, but without agar). After 1 day at 28° C., the cells were harvested in the exponential phase ($5-7.10^7$ cells/ml.), and separated from the culture medium and the pool of cells was extracted in a water bath. The dry weight was also determined.

The lysine concentration in the pool was determined by the Shimura and Vogel method (BPA, 1966, 118, 396). The best results were obtained with the mutant Mg-5, the pool of which contained 180 $\mu$mols of lysine per gram of dry weight, whereas the pool of IFP 29 contains 80 $\mu$mols.

b. Cultivation and Production of Acids

A typical gelose containing Candida lipolytica Mg-5 cells (ATCC 20-462) made resistant to concentrations of $10^{-3}$ M of trans-4-dehydrolysine was used for seeding a 100 ml. flask containing 20 ml. of a liquid medium A having the following composition:

| $KH_2PO_4$ | 3.4 g./l. |
|---|---|
| $Na_2HPO_4.12H_2O$ | 1.5 g./l. |
| $MgSO_4.7H_2O$ | 0.7 g./l. |
| $(NH_4)_2SO_4$ | 4 g./l. |
| $CaCl_2$ | 0.1 g./l. |
| $FeSO_4.7H_2O$ | 2 mg./l. |
| $CuSO_4.5H_2O$ | 5 $\mu$g./l. |
| $H_3BO_3$ | 10 $\mu$g./l. |
| $MnSO_4.7H_2O$ | 10 $\mu$g./l. |
| $ZnSO_4.7H_2O$ | 10 $\mu$g./l. |
| $(NH_4)_6Mo_7O_{24}.4H_2O$ | 100 $\mu$g./l. |
| $Co(NO_3)_2.6H_2O$ | 10 $\mu$g./l. |
| Yeast extract | 100 mg./l. |
| Tap water, | to make up to 1 litre |
| $C_{12}-C_{19}$ n-paraffin fraction | 15 g./l. |

The Candida cells were incubated at 30° C. after the flask containing the inoculum had been secured on an agitation table rotating at 140 r.p.m.

After incubation for 36 hours, 10 ml. of the inoculum were used to seed a 1.5-liter Fernbach flask containing 200 ml. of nutrient medium A.

After incubation for 36 hours at 30° C. on the agitation table, the 200 ml. of medium containing the growing Mg-5 cells were used to seed a fermentor having a capacity of 4 l. and containing two liters of nutrient medium A, the pH being adjusted by the addition of 4 N aqueous ammonia solution.

The medium was agitated at 2000 r.p.m. at 30° C. and the pH was maintained at 5, the n-paraffin layer being injected continuously into the fermentor at an average rate of 2.5 ml./hour.

After cultivation for 150 hours, the total quantity of hydrocarbons introduced was 140 g./l., whereas the concentration of excreted products in the fermentation medium was:

| Citric acid: | 135 g./l. |
|---|---|
| Isocitric acid: | 40.5 g./l. |
| Glutamic acid: | 1.8 g./l. |

The biological substance collected was found to contain 14 – 15% L-lysine with respect to the proteins, measured on hydrolysed cells using a JEOL automatic amino-acid analyser.

By way of comparison, Candida cells which had not been made resistant to a toxic analogue of L-lysine were cultivated under the same conditions. The quantities of citric, isocitric and glutamic acids excreted into the fermentation medium were nil or less than 1 gram, whereas the proportion of lysine with respect to the cellular proteins was 8 – 9%.

EXAMPLE 2

The fermentation process described in Example 1 was repeated with comparable results, using Candida lipolytica cells made resistant to amino-3-cyclohexylalanine, S-$\beta$-amino-ethyl cysteine, 2,6-diamino heptanoic acid, oxalysine, amino-3-methyl cyclohexane glycine, aza-4-lysine, 5-methyllysine, $\alpha$-amino-$\epsilon$-hydroxycaproic acid and $\delta$-hydroxylysine, by a method similar to that described in Example 1(a).

EXAMPLE 3

The preliminary culture, which was produced as described in Example 1, was inoculated in a 4 liter fermentor containing 2 liters of medium A having the composition given in Example 1(b).

The $C_{12}-C_{20}$ n-paraffin fraction was added to the medium so that its concentration was 15 g./l. and cultivation was begun at 30° C. and pH 5, which was maintained by adding 4 N ammonia with aeration.

After cultivation for 40 hours, the dry weight was found to be approximately 25 g./l. At this moment, continuous cultivation was begun by injecting medium A and $C_{12}-C_{20}$ hydrocarbons at the rate of 3 g./l. per hour, while an equal volume of culture medium was withdrawn.

The dilution rate was 0.070; the productivity per hour was 0.87 g./l. of cells and 0.49 g./l. of citric acid.

Note that the dilution ratio is the ratio for a given fermentation region.

The rate of introduction (or of withdrawal) of fermentation medium is expressed in volumes per hour/volume of reactor. It is therefore the reciprocal of a residence time.

EXAMPLE 4

A preliminary cultivation was performed as in Example 1. It was used to inoculate a "stage 1" reactor having a capacity of 4 liters and containing 3 l. of nutrient medium b; cultivation was begun as at the beginning of Example 3.

After cultivation for 40 hours at pH 4.5 and 30° C., the medium was continuously circulated from the moment when the dry weight was approximately 25 g./l. The dilution ratio adopted was 0.0.5 h$^{-1}$. The output of hydrocarbons per hour was 1.5 g./liter.

The culture medium was withdrawn at a rate equal to the feed rate. Under these conditions, the first stage stabilised at a concentration of 10.2 g./l. of cells and 1.3 g./l. citric acid.

The medium withdrawn from the first stage was transferred to a second or "excretion-stage" fermentor having a useful volume of 6 liters.

The second fermentor contained a medium having the same composition as medium A. When the injection of yeasts into the second stage began, n-paraffins were injected at a rate of 0.4 g./liter per hour.

The medium was withdrawn at a rate equal to the feed rate. The second fermentor stabilised at a concentration of 17 g./l. of cells and at a dilution ratio of 0.03 h$^{-1}$.

The effluent continuously withdrawn from the outlet of the second stage contained 15.5 g./l. citric acid.

Consequently, the overall productivity per hour was 0.46 g./l. citric acid and 0.51 g./l. of cells.

We claim:

1. A method for preparing a yeast enriched in L-lysine and capable of excreting an organic acid comprising:
    subjecting a wild yeast of the species *Candida Lipolytica* which is sensitive to the action of transdehydrolysine to the action of a mutagenic agent,
    cultivating the thus treated yeast in a culture medium containing transdehydrolysine in a concentration which is about 50 to 100 times greater than that to which the cells of the wild yeast are sensitive and so selecting the resistant yeast,
    and cultivating the resistant yeast on a medium containing at least one hydrocarbon.

2. The method of claim 1, wherein the mutagenic agent is a chemical agent.

3. The method of claim 1, wherein the mutagenic agent is radiation.

4. The method of claim 1, wherein the medium containing at least one hydrocarbon contains at least one normal paraffin having 10 to 20 carbon atoms.

5. The method of claim 4, wherein the medium contains a source of assimilable nitrogen.

6. The method of claim 5, wherein the medium also contains cations and anions which facilitate the growth of the yeast.

7. The method of claim 1, wherein said resistant yeast is cultivated at a pH of 3 to 6 and a temperature of 25° to 30° C. in an agitated aerated medium containing at least one hydrocarbon.

8. The method of claim 1, wherein said resistant yeast is cultivated at a pH of 3 to 6 and a temperature of 25° to 30° C. in an agitated aerated medium containing at least one normal paraffin having 10 to 20 carbon atoms, a source of assimilable nitrogen and cations and anions which facilitate the growth of the yeast.

9. The method of claim 1, wherein at the end of the cultivation of said resistant yeast, the yeast rich in L-lysine is separated from the reaction medium which contains one or more useful organic acids and said acids are recovered from the reaction medium.

10. The method of claim 1, wherein said resistant yeast excretes citric acid during cultivation.

11. The method of claim 10, wherein said resistant yeast also excretes isocitric acid and glutamic acid.

* * * * *

UNITED STATES PATENT AND TRADEMARK OFFICE
CERTIFICATE OF CORRECTION

PATENT NO. : 3,986,933
DATED : October 19, 1976
INVENTOR(S) :

It is certified that error appears in the above—identified patent and that said Letters Patent are hereby corrected as shown below:

Assignee: delete "Institute Francais du Petrol, des Carburants et Lubrifints et Enterprise de Recherches et d'Activities Petrolieres Elf, Paris Rueil Malmaison, France"

and insert --Institute Francais du Petrole et Entreprise de Recherches et d, Activites Petrolieres E.R.A.P., Rueil-Malmaison, France--

Signed and Sealed this

Thirty-first Day of January 1978

[SEAL]

Attest:

RUTH C. MASON
Attesting Officer

LUTRELLE F. PARKER
Acting Commissioner of Patents and Trademarks